(12) United States Patent
Liu et al.

(10) Patent No.: US 11,220,525 B2
(45) Date of Patent: Jan. 11, 2022

(54) METHOD FOR DYNAMICALLY REMOVING RECOMBINANT HUMAN NERVE GROWTH FACTOR PRECURSOR BY HYDROPHOBIC INTERACTION CHROMATOGRAPHY

(71) Applicant: Xintrum Pharmaceuticals, Ltd., Jiangsu (CN)

(72) Inventors: Wenchao Liu, Nanjing (CN); Hongliang Sun, Nanjing (CN); Yi Zhang, Nanjing (CN); Yuesheng Wang, Nanjing (CN)

(73) Assignee: XINTRUM PHARMACEUTICALS, LTD., Nanjing (CN)

( * ) Notice: Subject to any disclaimer, the term of this patent is extended or adjusted under 35 U.S.C. 154(b) by 0 days.

(21) Appl. No.: 17/030,281

(22) Filed: Sep. 23, 2020

(65) Prior Publication Data

US 2021/0002327 A1  Jan. 7, 2021

Related U.S. Application Data

(63) Continuation of application No. PCT/CN2018/114508, filed on Nov. 8, 2018.

(30) Foreign Application Priority Data

Mar. 26, 2018 (CN) .......................... 201810253682.5

(51) Int. Cl.
*C07K 5/00* (2006.01)
*C07K 1/20* (2006.01)
*C12N 5/071* (2010.01)
*C07K 14/48* (2006.01)

(52) U.S. Cl.
CPC .............. *C07K 1/20* (2013.01); *C12N 5/0682* (2013.01); *C07K 14/48* (2013.01)

(58) Field of Classification Search
None
See application file for complete search history.

(56) References Cited

U.S. PATENT DOCUMENTS 8,436,152 B2 * 5/2013 Brinkman .......... C07K 14/8125
530/424

FOREIGN PATENT DOCUMENTS

| CN | 1237184 A  |   | 12/1999 |
|----|------------|---|---------|
| CN | 102702341  | * | 6/2012  |
| CN | 103130868 A |   | 6/2013  |
| CN | 103880943  | * | 1/2014  |
| CN | 103880943 A |   | 6/2014  |
| CN | 106478801 A |   | 3/2017  |
| CN | 108239146 A |   | 7/2018  |
| CN | 108467429 A |   | 8/2018  |

OTHER PUBLICATIONS

English translation of International Search Report and Written Opinion on WO2019184366 from Patentscope.

* cited by examiner

*Primary Examiner* — Jeanette M Lieb
(74) *Attorney, Agent, or Firm* — Lin Sun-Hoffman; Yong Chen; Liu Chen & Hoffman LLP

(57) ABSTRACT

A method for removing precursors in recombinant human nerve growth factor (rhNGF) by hydrophobic interaction chromatography (HIC) is provided, where a Chinese hamster ovary (CHO) cell culture is processed by column chromatography for preliminary purification, and the pretreated sample obtained therefrom is further processed in a HIC column by washing the sample and then eluting the HIC column.

7 Claims, 4 Drawing Sheets

US 11,220,525 B2

METHOD FOR DYNAMICALLY REMOVING RECOMBINANT HUMAN NERVE GROWTH FACTOR PRECURSOR BY HYDROPHOBIC INTERACTION CHROMATOGRAPHY

TECHNICAL FIELD

The present invention relates to protein purification and more particularly to a method for dynamically removing a recombinant human nerve growth factor precursor by hydrophobic interaction chromatography.

DESCRIPTION OF RELATED ART

Human nerve growth factor that is produced in Chinese hamster ovary (CHO) cells and expressed by genetic engineering (hereinafter also referred to as recombinant human nerve growth factor, or rhNGF) contains a variety of impurities and cannot be directly used without prior purification. The chromatography methods in the prior art, though capable of removing many process-related impurities in rhNGF (e.g., host cell proteins and nucleic acids), have difficulties in removing rhNGF precursors that emerge as product-related impurities, wherein rhNGF precursors are a major type of rhNGF variants. As these variants are generally produced along with mature rhNGF (with the precursor variants containing the rhNGF sequence and therefore having similar physical and chemical properties to the rhNGF product), and different degrees of processing result in precursors of different molecular weights, the complexity of purification is increased, making it difficult to purify rhNGF on a large scale.

rhNGF is synthesized in vivo in the form of a precursor, which includes a signal peptide, a pro-peptide, and a mature-rhNGF moiety. The pro-peptide has two partially conserved regions that are required for precursor expression, the formation of bioactive proteins by enzymatic hydrolysis, and the secretion of mature rhNGF, and that also contribute to the correct folding of proteins. rhNGF precursors form bioactive mature rhNGF after being hydrolyzed at particular sites with furin or prohormone convertase. Incomplete processing with furin or prohormone convertase leads to the formation of complete precursors and partial precursors, which are collectively referred to herein as precursor variants.

While the precursor variants have similar properties to the rhNGF product, differences in the following aspects between rhNGF and its precursor variants can be ascertained by the analysis technology as well as according to the properties of the precursors themselves: molecular weight (a precursor has higher molecular weight than the mature rhNGF), electric charge (rhNGF has a lower isoelectric point than its precursor variants), and hydrophobicity (a precursor variant includes glycosylation modifications and is therefore less hydrophobic than the mature rhNGF). Generally, these subtle differences cannot be identified unless a chromatography material having a relatively small particle size is used.

Currently, reports on the purification of rhNGF include the following:

Chinese Published Patent Application No. 102702341A uses a two-step method that involves cation exchange and a molecular sieve (Superdex 75) to prepare an rhNGF whose purity is higher than 98%. While it is suspected that the molecular sieve (Superdex 75) is used to remove precursor variants, the patent application makes no mention of this. Moreover, as the molecular sieve requires highly concentrated samples, the loaded sample volume ranges only between 1% and 4% of the column volume, not to mention that the resin itself is expensive; consequently, the method is not suitable for large-scale industrial production.

Chinese Patent No. 1268639C uses hydrophobic interaction chromatography (hereinafter referred to as HIC) (preferably involving the use of the phenyl group) to remove precursors, and this method adopts the linear gradient elution approach.

Chinese Published Patent Application No. 106478801A uses a two-step method that involves cation exchange and HIC (preferably involving the use of the phenyl group) to prepare an rhNGF whose purity is higher than 99%, and the HIC used in this method also employs linear gradient elution. Linear gradient elution generally necessitates a two-pump chromatography system and therefore has rather strict requirements for the equipment, which is nevertheless disadvantageous to large-scale industrial production.

None of the foregoing methods uses HIC to separate an rhNGF precursor from the mature rhNGF, let alone remove a precursor variant by stepwise dynamic washing prior to the chromatography process.

SUMMARY OF THE INVENTION

One objective of the present invention is to provide a method for removing a precursor in rhNGF.

The inventors of the present invention analyzed the physical and chemical properties of rhNGF and its precursors. NGF precursors include glycosylation modifications, but mature rhNGF does not. The precursors include sugar chains and are therefore less hydrophobic than the mature rhNGF. Taking advantage of this property, the present invention not only separates rhNGF precursors from mature rhNGF by HIC, but also removes precursor variants by stepwise washing through HIC. In addition, the present invention uses a dynamic washing approach to enhance the efficiency of rhNGF purification. The operation method is detailed as follows:

A method for removing a precursor in rhNGF is characterized by the following steps:

1) Pretreating the raw material: A CHO cell culture is subjected to column chromatography once or for multiple times for preliminary purification, thereby obtaining a pretreated raw material for further chromatographic separation;

2) Washing the pretreated raw material: An HIC column is loaded with the substance obtained from step 1) in order to wash the pretreated raw material with a washing buffer and discard the precursor-containing eluate; and 3) Elution with an elution buffer, performed on the chromatography column on which step 2) has been carried out, thereby obtaining a purified rhNGF product.

The elution buffer is an aqueous solution of an alcohol or an aqueous solution of an alcohol and NaCl, the latter of which contains 7%-20% alcohol and 0-100 mM NaCl.

In step 1), the term "human nerve growth factor crude product" refers to the substance to be purified by the method of the present invention, is the product obtained by performing column chromatography for at least one time on the rhNGF expressed by a cell culture of CHO-cell-recombination host cells, and includes rhNGF precursors and other contaminants.

The present invention has no limitation on the column chromatography method used in step 1). All the column chromatography methods well known to a person skilled in the art can be used.

In step 2), precursors are removed by using higher electrical conductivity than that of the chromatography elution buffer in the next step, as well as a lower concentration of the alcohol solution in this step than the concentration of the chromatography elution buffer in the next step. More specifically, the washing buffer used in step 2) is an aqueous solution of an alcohol and NaCl and should satisfy the following conditions at the same time:

A. having a lower alcohol content than the elution buffer used in step 3);

B. having an NaCl content of 200~400 mM; and

C. being within the same pH range as the substance obtained from step 1).

The alcohol is preferably ethanol. The washing buffer used in the embodiments disclosed herein of the present invention contains 4%~6% ethanol (by volume).

In step 2), the washing adopts a "dynamic washing" approach, in which the washing volume is determined by the following linear equation of the peak area of the eluted product in the column chromatography in step 1):

Washing volume(in the unit of $CV$)=8.5−peak area/ml resin/1000.

The inventors of the present invention studied the materials used in HIC. It was found through experimentation that solid-phase HIC materials with relatively large particle sizes such as Octyl FF, Capto Butyl, Capto Phenyl HS, Butyl FF, and Phenyl FF from GE are not very effective in removing rhNGF precursors. The HIC medium used in the present invention has such ligands as the phenyl group or a butyl group and is preferably Butyl Sepharose High Performance.

DETAILED DESCRIPTION OF THE INVENTION

Figure 1:
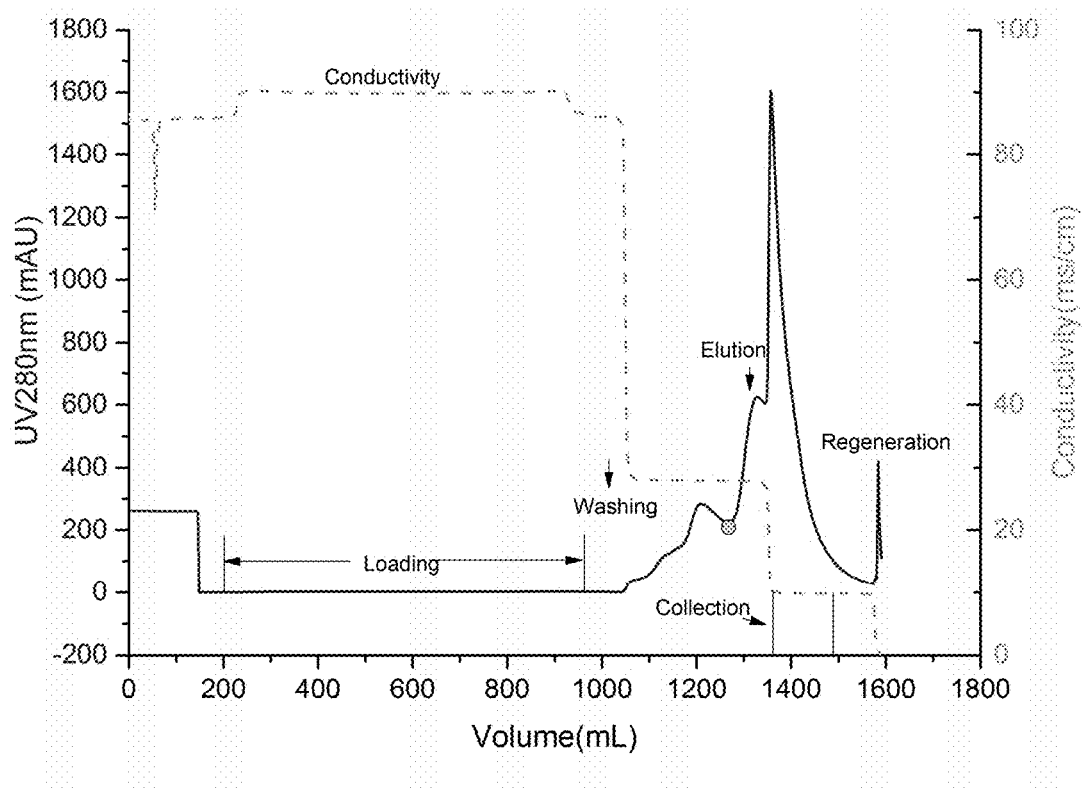
FIG. 1 shows a process for purifying rhNGF by HIC, wherein the process includes equilibration, loading, washing, and elution.

The following embodiments serve only to demonstrate the method and apparatus of the present invention and are not intended to be restrictive of the scope of the present invention.

The technical terms used herein are defined as follows:

"Recombinant human nerve growth factor (rhNGF)" refers to human nerve growth factor that is produced by a Chinese hamster ovary (CHO) cell and expressed by genetic engineering, wherein the expressed sequence includes the $1^{st}$-$118^{th}$ amino acids. During the expression process, a basic amino acid moiety at the C terminal may be cut off, resulting in molecules whose sequence includes only the $1^{st}$-$117^{th}$ amino acids; as a result, complexes composed of molecules whose sequences include only the $1^{st}$-$117^{th}$ amino acids and molecules whose sequences include the $1^{st}$-$118^{th}$ amino acids are formed.

"rhNGF precursor" refers to any of a series of proteins that are expressed from the same rhNGF gene and are formed by post-translational modification during intracellular secretion, or by the chemical reaction of an amino acid residue side chain after secretion, or by the degradation of a peptide chain.

"Precursor" refers to an unprocessed or partially processed form of an expressed rhNGF. Human nerve growth factor is generally synthesized in vivo in the form of precursors. The precursors form bioactive mature rhNGF after being hydrolyzed at particular sites with furin or prohormone convertase. A precursor herein may be a complete precursor or a partial precursor but is always glycosylated.

"Hydrophobic interaction chromatography (HIC)" refers to a method of separation enabled by the reversible binding between the hydrophobic ligands coupled to a stationary-phase carrier and some hydrophobic molecules in the mobile phase. Commercially available HIC materials include agarose with an immobilized phenyl group, butyl group, or tert-butyl group, and polymethyl methacrylate (PMMA) with an immobilized phenyl group, butyl group, or ether group.

"Load" refers to the crude product loaded on an HIC material.

"Buffer" refers to a solution that, through the reaction between paired acid and alkaline ingredients, can resist pH variation.

"Equilibration buffer" refers to a buffer that is used to equilibrate an HIC material before the HIC material is loaded with a crude product.

"Washing buffer" refers to a buffer that is allowed to flow through an HIC material after the HIC material is loaded with a crude product and before the protein of interest is eluted.

"Elution buffer" refers to a buffer that is used to elute rhNGF from a solid phase.

A "regeneration buffer" can be used to regenerate an HIC filler so that the filler can be used again. The electrical conductivity and pH value of a regeneration buffer enable the buffer to remove virtually all the contaminants and rhNGF on an HIC filler.

"Electrical conductivity" refers to the ability of an aqueous solution to conduct electric current between two electrodes. The electrical conductivity of a solution can be changed by varying the ion concentration of the solution.

"To load" refers to allowing a crude product to flow through an HIC material so that rhNGF and certain contaminants are bound to the HIC material.

"Overhead washing" refers to the process of washing an HIC column with an equilibration buffer after the column is loaded with a crude product, the objective being to wash the crude product out of the column.

"Washing" refers to the process of a washing buffer flowing through an HIC material, and generally refers to the removal of contaminants.

"Elution" refers to the process of an elution buffer flowing through an HIC material, and generally refers to the obtainment of a desired product.

MES is 2-(N-morpholino)ethanesulfonic acid. MOPSO is 3-(N-morpholino)-2-hydroxypropanesulfonic acid. SEC- HPLC is size-exclusion high-performance liquid chromatography. PB refers to a phosphate buffer.

An HIC-based purification method according to the present invention generally includes the steps, to be sequentially performed, of: (1) equilibrating an HIC material; (2) loading the HIC material with a crude product; (3) performing overhead washing with an equilibration buffer; (4) performing intermediate washing with a washing buffer; and (5) eluting the desired rhNGF with an elution buffer.

The present invention uses HIC so that rhNGF precursors (mainly precursors) can be washed under various mobile-phase conditions. The mobile-phase conditions include lowering the concentration of a salt and may also include increasing the concentration of a polar solvent. pH affects the binding between rhNGF and resin, too, and a neutral pH value is preferably used. While implementing the present invention, the buffer salt in the buffers may be sodium acetate, a phosphate, MES, or MOPSO, and it is preferable that a phosphate is used as the buffer salt. The elution salt used in the buffers may be, but is not limited to, sodium chloride, sodium acetate, potassium chloride, or ammonium sulfate, and it is preferable that sodium chloride is used as the elution salt. The organic solvent used in the buffers may be, but is not limited to, ethanol, propylene glycol, ethylene glycol, or hexamethylene glycol, and it is preferable that ethanol is used as the organic solvent.

Generally, the equilibration buffer is allowed to flow through the HIC material before the HIC material is loaded with the crude product, which contains rhNGF and one or more molecular variants of rhNGF. In one preferred embodiment of the present invention, the equilibration buffer has a pH value of about 5.5 to about 7.0, such as about 6.0. An excessively low pH value (e.g., lower than 5.0) will enhance the hydrophobic effect. The salt concentration of the equilibration buffer is controlled at about 0.8 M to 1.2 M NaCl, such as about 1.1 M NaCl. An illustrative equilibration buffer contains 20 mM MES and 1.1 M NaCl and has a pH value of 6.0. Another illustrative equilibration buffer contains 20 mM PB and 1 M NaCl and has a pH value of 7.0.

Once equilibrium is achieved, the HIC material is loaded with the crude product, which contains rhNGF and one or more molecular variants of rhNGF. The crude product has a pH value ranging from 5.5 to 7.0, such as 6.0 or 7.0, and a salt concentration controlled at about 0.8 M to 1.2 M NaCl, such as about 1.1 M NaCl. In one embodiment, the HIC material is loaded with a crude product obtained from HIC elution, and the loading density is about 5~10 g/L resin in order for rhNGF and its precursors to bind to the HIC filler.

After loading, overhead washing is carried with the equilibration buffer. The overhead washing conditions are identical to the conditions of the equilibration step. Generally, the overhead washing volume is 2~3 times the column volume.

When overhead washing is completed, the HIC material is washed with the washing buffer. During the washing process, the washing buffer flows through the HIC material. The composition of the washing buffer is generally so chosen as to elute as large an amount of impurities (e.g., molecular variants such as precursors) from the resin as possible, but not to elute the desired rhNGF. The pH value of the washing buffer is controlled between 5.5 and 7.0, such as at about 6.0 or 7.0; the salt concentration of the washing buffer is controlled between about 0.2 and about 0.4 M NaCl, such as at about 0.25 M; and the organic solvent in the washing buffer is controlled at about 4% to about 6% ethanol, such as about 5% ethanol. The washing volume is dynamically controlled and is determined by the elution peak area in the chromatography step immediately before the HIC step, generally 5~7 CV. It is preferable that the washing buffer contains 20 mM PB, 0.4 M NaCl, and 6% ethanol and has a pH value of 6.0, or that the washing buffer contains 20 mM PB, 0.25 M NaCl, and 5% ethanol and has a pH value of 7.0.

After the washing step, the desired rhNGF is eluted from the HIC material. The elution of rhNGF can be achieved by lowering the salt concentration or increasing the organic solvent concentration. In one embodiment, the elution buffer contains about 0 to about 100 mM NaCl and about 7% to about 20% ethanol. In most cases, the elution buffer has generally the same pH value as the washing buffer. One preferred elution buffer contains 20 mM PB, 0.1 M NaCl, and 7% ethanol and has a pH value of 7.0. Another preferred elution buffer contains 20 mM PB and 20% ethanol and has a pH value of 6.0.

While the HIC-based purification method disclosed herein may include other steps, it is preferable that the method is composed only of the following steps: equilibration; loading of the crude product, which contains rhNGF and its molecular variants; the washing step for eluting the molecular variants; and the elution step for eluting the rhNGF.

If necessary, the rhNGF preparation obtained by the HIC method disclosed herein may be further purified. Illustrative further purification steps have been discussed above.

Embodiment 1: HIC of rhNGF 1.1 Overall Process

A chromatography column was operated in the binding-eluting mode at ambient temperature. The chromatography column used Butyl Sepharose High Performance (which is a resin composed of a highly cross-linked agarose matrix coupled with the butyl functional group) as the HIC resin and was filled with the HIC resin to a bed height of 9~11 cm. Before loading with an ion-exchange chromatography eluted product, the storage liquid in the chromatography column was washed away with the equilibration buffer, which also equilibrated the column. The equilibrated chromatography column was then loaded with the ion-exchange chromatography eluted product in order for the product to bind to the resin. After loading, overhead washing was carried out with the equilibration buffer to wash off the unbound load. Once the overhead washing was completed, the column was washed with the washing buffer to remove molecular variants. Then, elution was performed with an elution buffer, whose volume was 3 CV at most, and the eluted product was collected. After elution, the column was cleaned with the regeneration buffer (20% ethanol) and a cleaning liquid (0.5 N NaOH) and was subsequently stored in the storage liquid until the next use (see FIG. 1).

Table 1 shows the process conditions of the HIC process of rhNGF according to the present invention.

TABLE 1

HIC process of rhNGF

| Stage | Buffer/solution | Process parameter | Flow velocity (cm/hr) |
|---|---|---|---|
| Column bed height | N/A | 10 cm | N/A |
| Equilibration | 20 mM MES/1.1M NaCl, pH | 4 CV | 100 |

TABLE 1-continued

HIC process of rhNGF

| Stage | Buffer/solution | Process parameter | Flow velocity (cm/hr) |
|---|---|---|---|
| Loading | Eluted product obtained by ion-exchange chromatography, with electrical conductivity higher than 70 mS/cm 7.0 | 5~10 g rhNGF/L resin | 100 |
| Overhead washing | 20 mM MES/1.1M NaCl, pH 7.0 | 2 CV | 100 |
| Washing | 20 mM PB/0.25M NaCl/5% ethanol, pH 7.0 | 6 CV | 100 |
| Elution | 20 mM MES/0.1M NaCl/7% ethanol, pH 7.0 | 3 CV | 100 |
| | Start of product collection | Electrical conductivity slope smaller than −2.999 | N/A |
| | End of product collection | UV280 100~150 mAU | N/A |
| Regeneration | 20% ethanol | 2 CV | 100 |
| Cleaning | 0.5N NaOH | 3 CV | 50 |
| Storage | 20% ethanol | 2 CV | 50 |

1.2 Dynamic Control of Intermediate Washing Volume

Figure 2:
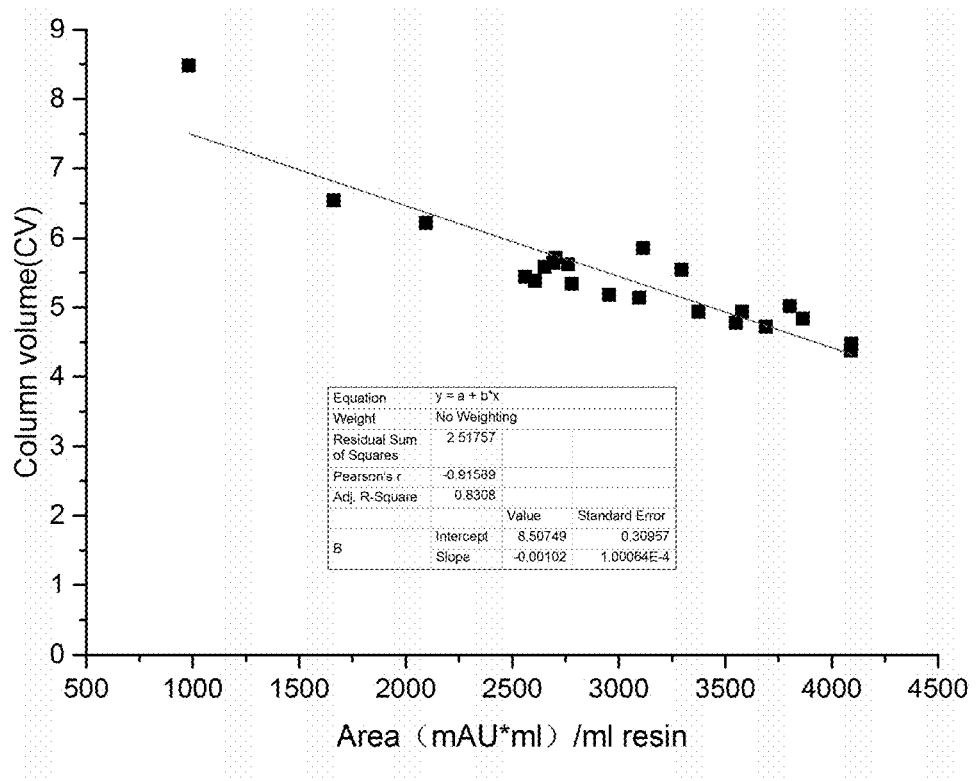
FIG. 2 shows the relationship between the peak areas of pre-HIC samples and the washing volumes measured in CV. The plot illustrates the relationship between the peak areas of the eluted samples in the step immediately before HIC and the washing volumes used in HIC. The larger the peak area, the smaller the washing volume.

The washing volume in the isocratic washing process was variable with the loaded sample volume, and there was a particular relationship between the loaded sample volume and the intermediate washing volume. The loaded sample volume was substituted by the peak area of the eluted sample in the step preceding HIC, and this allowed the decision regarding the intermediate washing volume to be made online in real time. The washing volume corresponding to the first valley (indicated by the circle in FIG. 1) of the washing process was used as the datum, and the data of multiple batches of HIC-based purification was analyzed to obtain the washing volumes and the peak area of each eluted sample in the step before HIC. The relationship between the washing volumes and the peak areas is plotted in FIG. 2. As can be seen in FIG. 2, the largest washing volume was 8.5 CV, and the washing volume decreased as the loaded sample volume increased. Generally, the normal washing volume should be larger than the volume corresponding to the first valley.

1.3 Analysis and Comparison of Samples Before and After Chromatography

Figure 3:
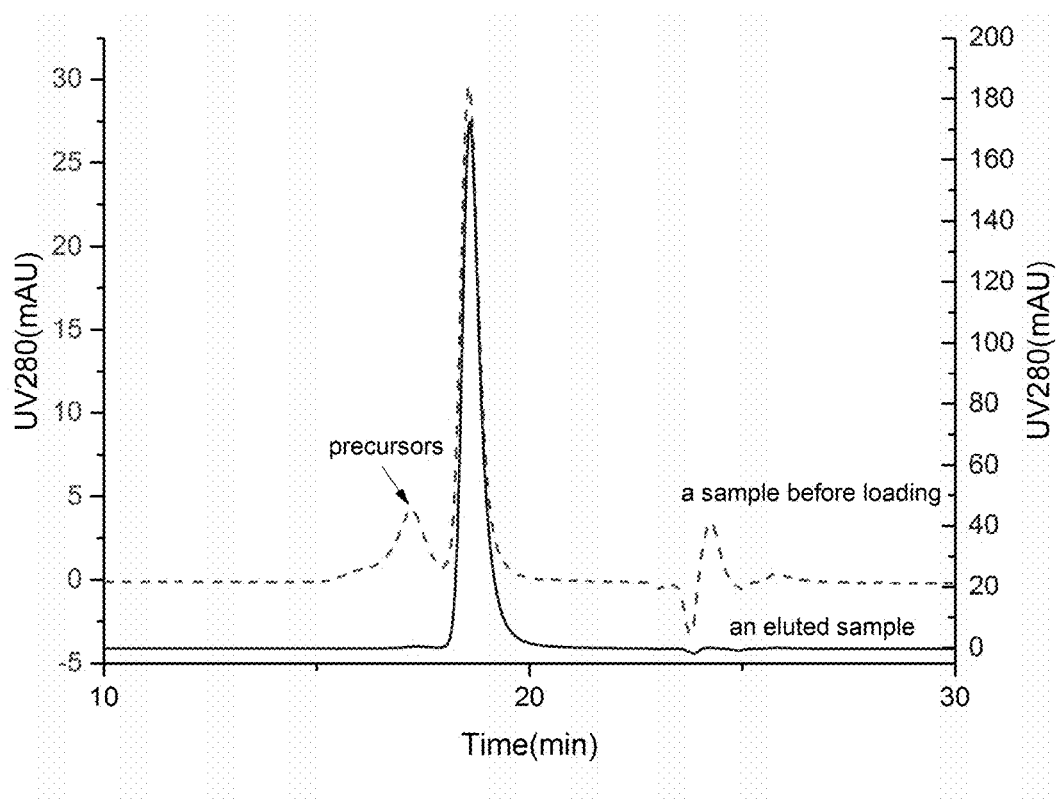
FIG. 3 shows the SEC-HPLC analysis results of a sample before loading and of an eluted sample. The plot provides the SEC-HPLC analysis results of samples taken from the HIC process. The analysis results show that the washing process removed most of the precursor variants.

The rhNGF recovery rate and the precursor variant removal rate were analyzed by the SEC-HPLC method. The chromatography column used was the TSK gel G2000SWXL column (7.8×300 mm). The mobile phase was a 0.15 M-dibasic sodium phosphate and 0.1 M-sodium dihydrogen phosphate solution/acetonitrile (in a volume ratio of 85:15). During the analysis, the loaded sample volume was 20 μL, flow velocity was 0.5 mL/min, column temperature was 25 degrees, and the detection wavelength was 280/214 nm. The analysis lasted for 40 min. Proportions were calculated by the area normalization method. As the solution system was mild and did not cause dissociation of the two subunits of the rhNGF, the peak corresponded to the dimer. The SEC-HPLC method distinguished the mature rhNGF from its precursor variants relatively well. The SEC-HPLC analysis results of the sample before loading for purification and after elution are presented in FIG. 3. As can be seen in FIG. 3, the precursor variants in the product were removed by the purification process of the present invention.

1.4 Statistical Data Analysis

Figure 4:
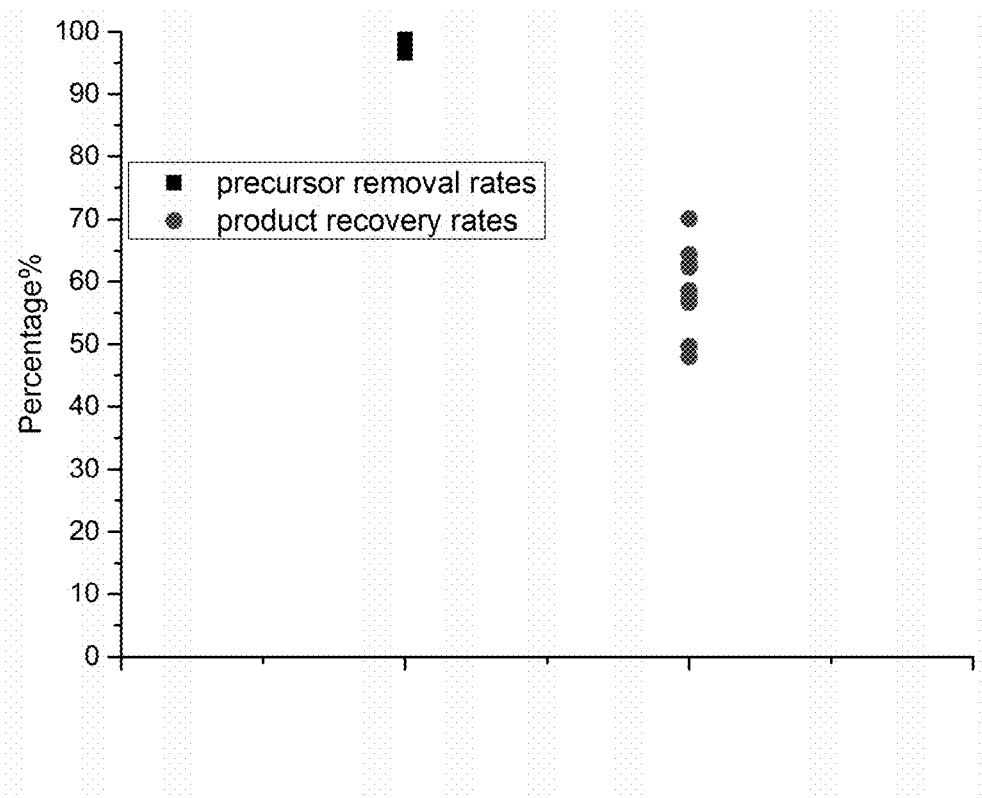
FIG. 4 shows a summary of precursor removal rates and product recovery rates. The plot provides the statistical analysis results of multiple batches of HIC-based purification. The analysis results show high precursor variant removal rates and high product recovery rates, indicating that the present invention has good process performance.

The precursor removal rate and the product recovery rate were calculated as follows, based on the SEC-HPLC analysis results of the to-be-loaded crude product and the eluted product: precursor variant removal rate=(1− the proportion of precursor variants in the eluted product/the proportion of precursor variants in the to-be-loaded crude product)×100%; product recovery rate=(main peak area of the eluted product per unit sample input amount×eluting volume)/(main peak area of the to-be-loaded crude product per unit sample input amount×loaded sample volume)×100%. The data of multiple batches of HIC-based purification was analyzed, and the analysis results are shown in FIG. 4. The aforesaid process conditions led to a precursor variant removal rate of 98.0%±0.9% and a recovery rate of 58%±7%, indicating good process performance.

What is claimed is:

1. A method for removing a precursor in recombinant human nerve growth factor (rhNGF) by hydrophobic interaction chromatography (HIC), comprising:
   1) processing a Chinese hamster ovary (CHO) cell culture by column chromatography for preliminary purification, thereby obtaining a product for further chromatographic separation;
   2) loading the product obtained from step 1) in a HIC column, washing the product with a washing buffer and discarding the eluate containing the precursor, wherein the washing buffer comprises an alcohol and NaCl, and; and
   3) eluting the HIC column used in step 2) using an elution buffer, thereby obtaining a purified rhNGF product;
   wherein said washing buffer satisfies each of the following conditions:
   A. having higher electrical conductivity than the chromatography elution buffer in step 3;
   B. having a lower alcohol content than the chromatography elution buffer in step 3); and
   C. being within a same pH range as the product obtained from step 1); and
   wherein said washing in step 2) comprises using a washing volume which is determined by the following linear equation of a peak area of the product obtained from step 1): washing volume (in the unit of CV)=8.5- the peak area/ml resin/1000.

2. The method of claim 1, wherein said alcohol is ethanol.

3. The method of claim 1, wherein said washing buffer has an ethanol content of from 4% to 6% by weight.

4. The method of claim 1, wherein said washing buffer has an NaCl content of from 200 to 400 mM.

5. The method of claim 1, wherein said elution buffer in step 3) comprises an alcohol, or is an aqueous solution comprising an alcohol and NaCl.

6. The method of claim 5, wherein said elution buffer has an ethanol content of from 7% to 20% by weight.

7. The method of claim 5, wherein said elution buffer has a NaCl content of from 0 to 100 mM.

* * * * *